(12) United States Patent
Kobayashi et al.

(10) Patent No.: US 12,186,899 B2
(45) Date of Patent: Jan. 7, 2025

(54) ASSIST DEVICE

(71) Applicant: JTEKT CORPORATION, Osaka (JP)

(72) Inventors: Yuki Kobayashi, Nara (JP); Akihisa Umetani, Nara (JP); Mitsuharu Ozaki, Kashiba (JP)

(73) Assignee: JTEKT CORPORATION, Kariya (JP)

( * ) Notice: Subject to any disclaimer, the term of this patent is extended or adjusted under 35 U.S.C. 154(b) by 870 days.

(21) Appl. No.: 17/201,401

(22) Filed: Mar. 15, 2021

(65) Prior Publication Data

US 2021/0291354 A1 Sep. 23, 2021

(30) Foreign Application Priority Data

Mar. 18, 2020 (JP) .................................. 2020-048263

(51) Int. Cl.
*B25J 9/00* (2006.01)
*A61F 5/01* (2006.01)
*A61H 1/02* (2006.01)

(52) U.S. Cl.
CPC ........... *B25J 9/0006* (2013.01); *A61F 5/0125* (2013.01); *A61H 1/0244* (2013.01); *A61H 2201/1645* (2013.01); *A61H 2201/165* (2013.01); *A61H 2201/1671* (2013.01)

(58) Field of Classification Search
CPC ............ B25J 9/0006; A61H 2003/007; A61H 2201/1671; A61H 2201/1645; A61F 5/0125
See application file for complete search history.

(56) References Cited

U.S. PATENT DOCUMENTS

| 4,969,452 | A | * | 11/1990 | Petrofsky | A61F 5/0125 |
| | | | | | 602/26 |
| 9,808,073 | B1 | * | 11/2017 | Maxwell | A61H 3/008 |
| 2006/0064047 | A1 | * | 3/2006 | Shimada | A61F 5/0102 |
| | | | | | 602/26 |
| 2011/0172570 | A1 | * | 7/2011 | Shimizu | A61H 3/00 |
| | | | | | 601/35 |

(Continued)

FOREIGN PATENT DOCUMENTS

| JP | 2006-87477 A | 4/2006 |
| JP | 2016-59763 A | 4/2016 |
| JP | 2018-199205 A | 12/2018 |

OTHER PUBLICATIONS

Japanese Office Action issued Oct. 24, 2023 in Japanese Application 2020-048263, (with partial unedited computer-generated English translation), citing documents 15-16 therein, 6 pages.

*Primary Examiner* — Justine R Yu
*Assistant Examiner* — Gwynneth L Howell
(74) *Attorney, Agent, or Firm* — Oblon, McClelland, Maier & Neustadt, L.L.P.

(57) ABSTRACT

An assist device includes: a first brace configured to be worn on at least a waist of a user; an arm configured to extend along a thigh of the user and to rotate with respect to the first brace; an actuator configured to generate torque that rotates the arm; and a second brace provided on the arm and configured to be worn on the thigh. The arm includes an arm body and a holding portion. The holding portion is provided on the arm body such that the holding portion is movable in a longitudinal direction of the arm body. The holding portion holds the second brace such that the second brace is rotatable.

5 Claims, 10 Drawing Sheets

(56) References Cited

U.S. PATENT DOCUMENTS

| | | | |
|---|---|---|---|
| 2017/0112652 A1* | 4/2017 | Raab | A61F 5/0125 |
| 2018/0200878 A1* | 7/2018 | Tsai | A61F 2/70 |
| 2018/0272525 A1* | 9/2018 | Kumeno | B25J 9/1638 |
| 2018/0325764 A1* | 11/2018 | Yagi | B25J 9/0006 |
| 2020/0179218 A1 | 6/2020 | Katoh et al. | |
| 2020/0268585 A1* | 8/2020 | Luo | A61H 3/00 |
| 2021/0052459 A1* | 2/2021 | Belanger-Desbiens | B25J 9/0006 |

\* cited by examiner

ASSIST DEVICE

CROSS-REFERENCE TO RELATED APPLICATION

This application claims priority to Japanese Patent Application No. 2020-048263 filed on Mar. 18, 2020, incorporated herein by reference in its entirety.

BACKGROUND

1. Technical Field

The disclosure relates to assist devices.

2. Description of Related Art

Various assist devices that are designed to be worn on the user's (human) body to help the user do his or her work have been proposed. The user wearing the assist device can work with small force (small burden) even when, e.g., lifting a heavy object. Such an assist device is disclosed in, e.g., Japanese Unexamined Patent Application Publication No. 2018-199205 (JP 2018-199205 A).

SUMMARY

The assist device disclosed in JP 2018-199205 A is configured to transmit the outputs of actuators (motors) to the right and left thighs of a user through arms to support movements of the right and left thighs with respect to the waist.

Braces configured to be worn on the user's thighs are provided on the arms. Each brace has belts etc. fixed to the arm and configured to be wrapped around and fastened to the thigh. The braces are contact points between the assist device and the user, and the assist force is transmitted to the user through the braces. The braces are therefore firmly secured to the thighs. Accordingly, the braces may not be able to follow the user's movements, which may cause the user to feel a pressure or rub on his or her thighs from the braces when the assist force is applied from the assist device. Moreover, it may be difficult for small or large users to put the braces on properly, which may cause the users to feel a pressure or rub on their thighs. Such a pressing or rubbing feeling may give the users a weird feeling or discomfort. The present disclosure reduces the weird feeling or discomfort that is given to a user.

An aspect of the disclosure is an assist device. The assist device includes: a first brace configured to be worn on at least a waist of a user; an arm configured to extend along a thigh of the user and to rotate with respect to the first brace; an actuator configured to generate torque that rotates the arm; and a second brace provided on the arm and configured to be worn on the thigh. The arm includes an arm body and a holding portion. The holding portion is provided on the arm body such that the holding portion is movable in a longitudinal direction of the arm body. The holding portion holds the second brace such that the second brace is rotatable.

According to the above configuration, the second brace configured to be worn on the thigh is held by the holding portion. The second brace is therefore held so as to be movable and rotatable with respect to the arm body. Accordingly, the second brace can be moved or rotated according to the body shape and movements of the user. This configuration reduces a pressing or rubbing feeling the second brace causes on the thigh when an assist force is applied from the assist device, and thus reduces a weird feeling or discomfort that is given to the user.

In the assist device, the second brace may include a pad having a plate shape. The arm body may include a guide rail extending in the longitudinal direction of the arm body. The holding portion may include a moving block, a base member, and a pad support portion. The moving block is configured to run on the guide rail in the longitudinal direction of the arm body. The base member is fixed to the moving block and includes a base surface extending in the longitudinal direction. The pad support portion supports the pad such that the pad is rotatable with the pad facing the base surface. The pad may have a slit extending in a circumferential direction about a rotation center of the second brace. The holding portion may further include a pin member protruding from the base surface and inserted in the slit. According to the above configuration, a rotation range of the second brace can be limited to a necessary range.

In the above assist device, the base member may have a bolt hole being open to the base surface and having in place a bolt that fixes the base member to the moving block. The pad may have an exposure hole configured to expose the bolt hole. With this configuration, even though the base surface is covered by the pad, the bolt can be inserted into and removed from the bolt hole that is open to the base surface through the exposure hole.

According to the above configuration, a weird feeling or discomfort that is given to the user is reduced.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Overall Configuration of Assist Device

Figure 1:
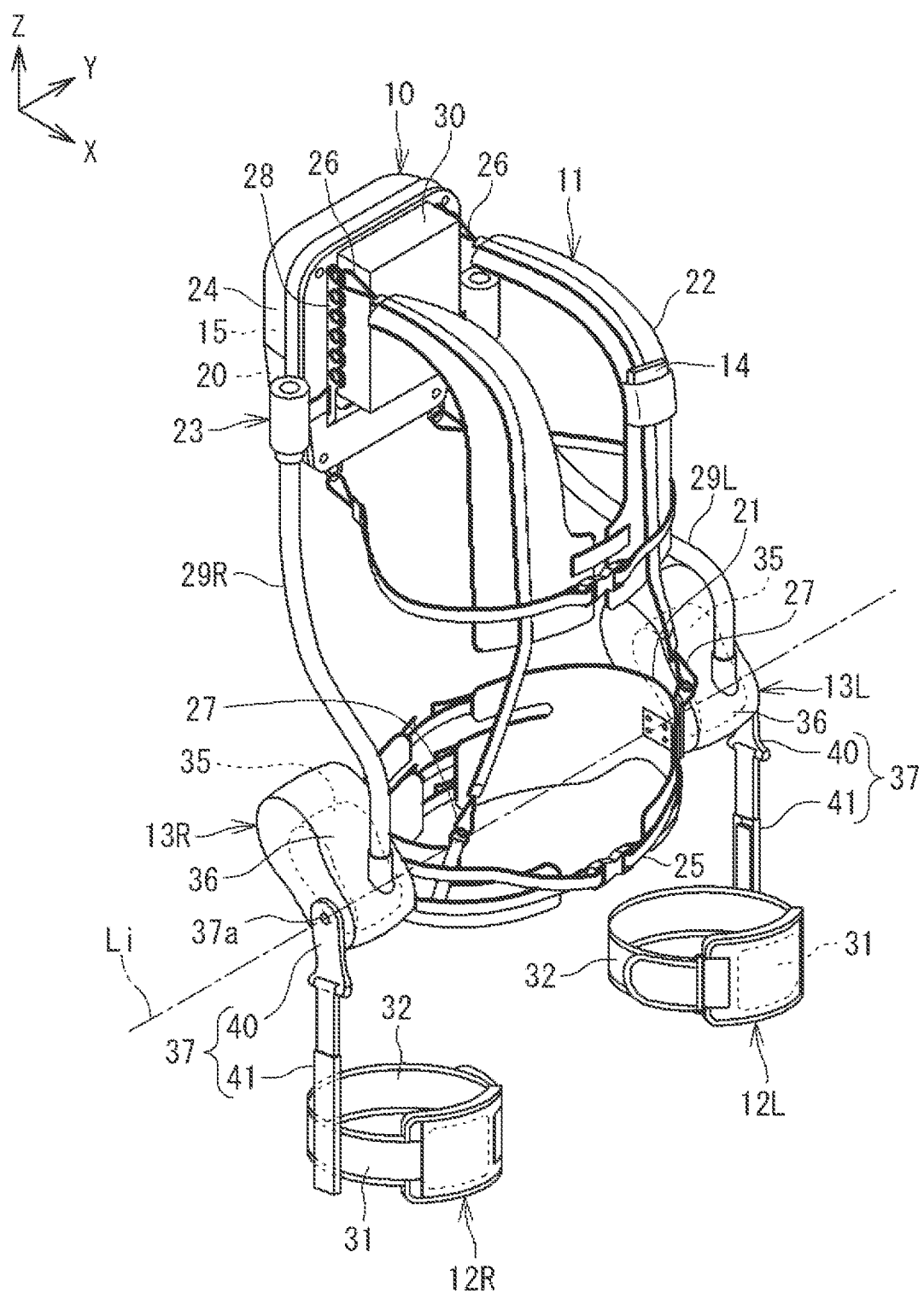
FIG. 1 is a perspective view illustrating the overall configuration of an assist device.
Figure 2:
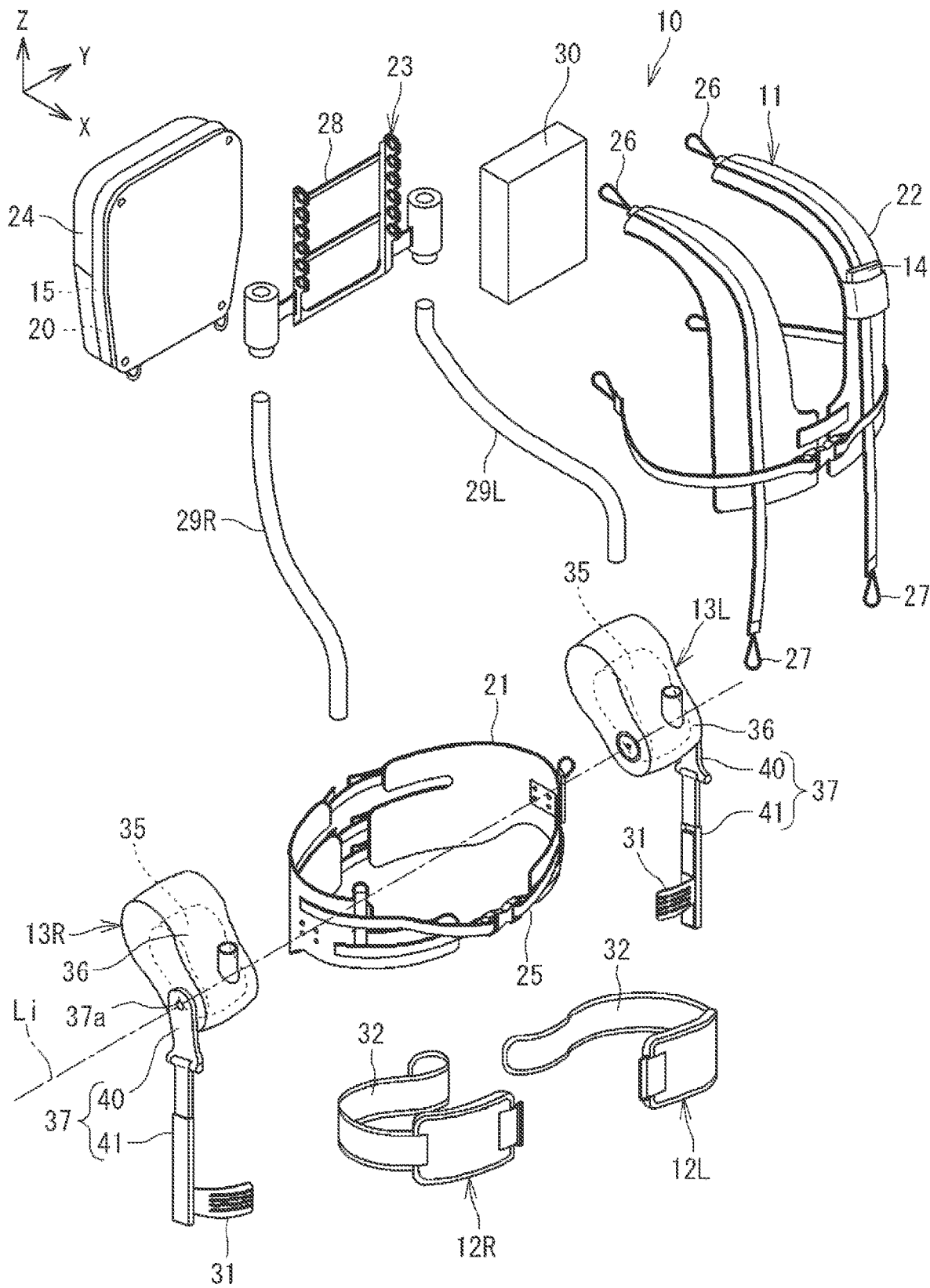
FIG. 2 is an exploded perspective view of the assist device of FIG. 1.
Figure 3:
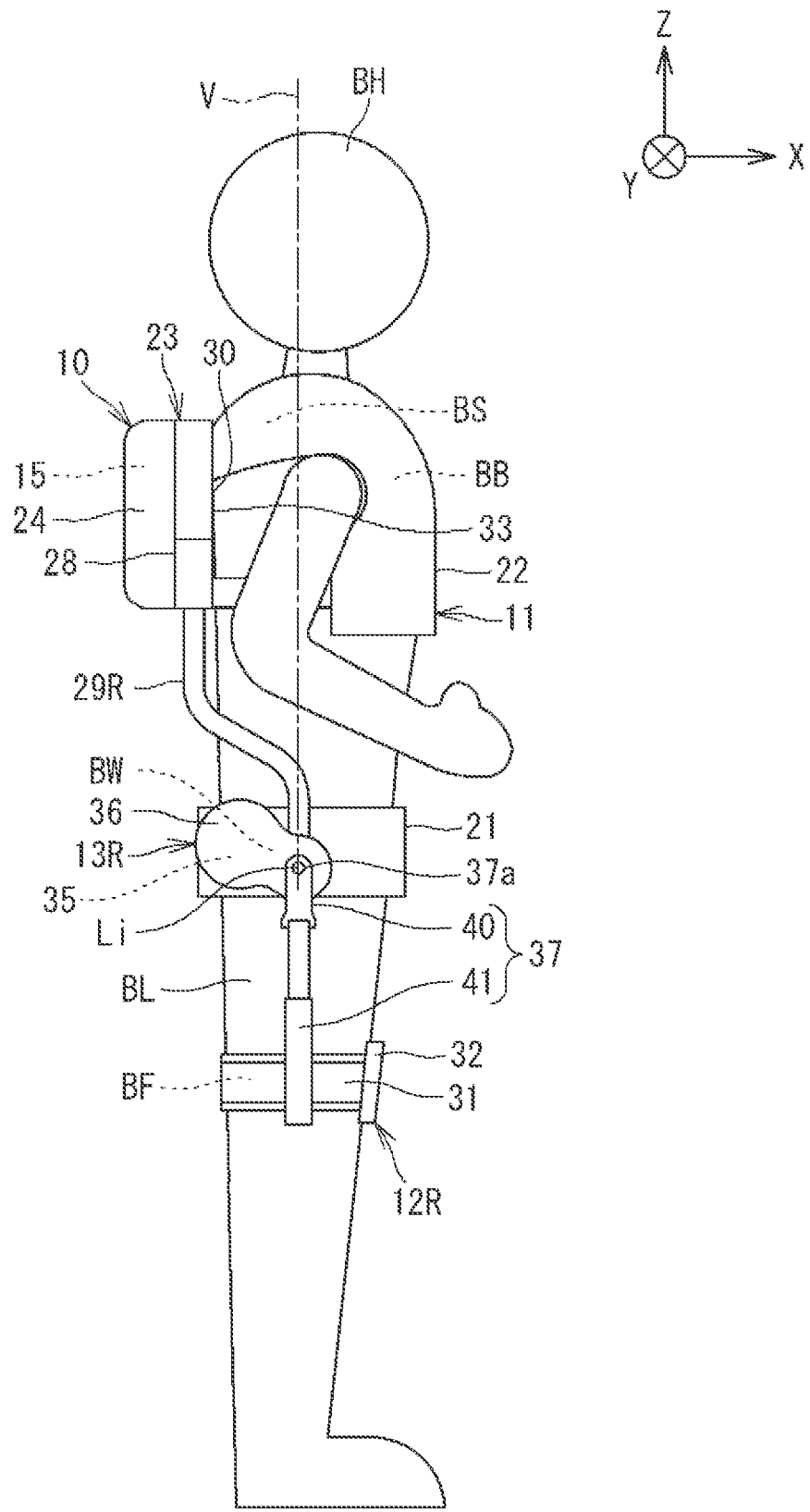
FIG. 3 is a side view of a user wearing the assist device of FIG. 1.
Figure 4:
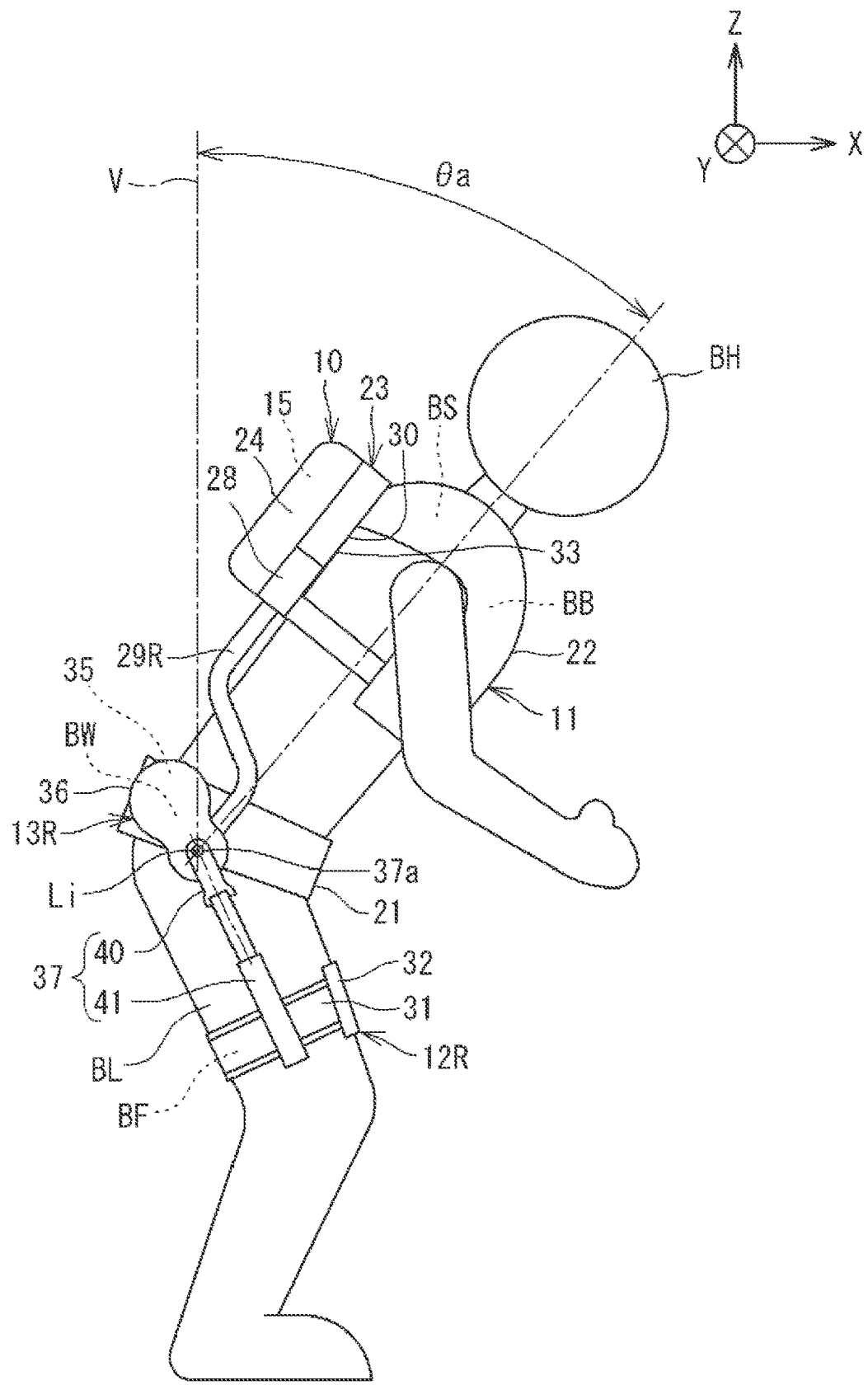
FIG. 4 is a side view of the user wearing the assist device of FIG. 1.

Preferred embodiments of the disclosure will be described with reference to the accompanying drawings. FIG. 1 is a perspective view illustrating the overall configuration of an assist device. FIG. 2 is an exploded perspective view of the assist device of FIG. 1. FIGS. 3 and 4 are side views of a user wearing the assist device of FIG. 1. The assist device is schematically illustrated in FIGS. 3 and 4. FIG. 3 illustrates the user in an upright posture, and FIG. 4 illustrates the user in a leaning forward posture. The upright posture shown in FIG. 3 is a posture in which the longitudinal direction of the user's upper body from a waist BW toward a head BH (the longitudinal direction of his or her spine) extends along a vertical line V. The leaning forward posture shown in FIG. 4 is a posture in which the longitudinal direction of the user's upper body is tilted forward. The leaning forward posture includes a posture with the user's legs BL bent as shown in FIG. 4 in addition to a posture with the user's legs BL straight (knees straight). In FIG. 4, θa represents the angle of the leaning forward posture of the user's upper body with respect to the vertical line V.

The assist device 10 is a device that supports the rotational movements of the thighs BF with respect to the waist BW of the user, for example, when he or she lifts a package and when the user lowers a package, and that supports the rotational movements of the thighs BF with respect to the waist BW of the user when he or she walks. The assist device 10's operation of assisting the user's body is herein referred to as the "assist operation."

The X, Y, and Z axes in the figures are perpendicular to each other. The X axis direction corresponds to the forward direction, the Y axis direction corresponds to the left direction, and the Z axis direction corresponds to the upward direction for the user wearing the assist device 10 and being in the upright posture. Regarding the assist operation, assisting in the rotational movements of the thighs BF with respect to the waist BW as described above is the same as assisting in the rotational movements of the waist BW with respect to the thighs BF. The assist operation is an assist operation of applying torque about an imaginary line Li in the lateral direction of the user passing through the user's waist BW to the user. This torque is herein sometimes referred to as the "assist torque."

The assist device 10 of FIG. 1 includes a first brace 11, right and left second braces 12R, 12L, and right and left actuator units 13R, 13L. The first brace 11 has a waist support portion 21 and a jacket portion 22 and is configured to be worn on the user's upper body including the waist BW. The right and left second braces 12R, 12L are configured to be worn on the user's right and left thighs BF. The right and left actuator units 13R, 13L are drive units that are attached between the first brace 11 and the second braces 12R, 12L and that are driven to perform the assist operation.

The assist device 10 further includes an operation unit 14 and a control device 15. The operation unit 14 is what is called a remote controller and is a device to which the user inputs the specifications of the assist operation etc. The specifications of the assist operation include the operation modes of the assist operation, the strength of the assist operation, the speed of the assist operation, etc. The operation modes include, e.g., "walking," "lowering," and "lifting." The operation unit 14 is provided with a select button that allows the user to select the specifications of the assist operation. The operation unit 14 is attached to, e.g., the jacket portion 22 of the first brace 11. The operation unit 14 and the control device 15 are connected wired or wireless and can communicate with each other. The control device 15 controls the operations of the actuator units 13R, 13L according to the information input to the operation unit 14.

The first brace 11 includes the waist support portion 21, the jacket portion 22, a frame 23, and a backpack portion 24. The waist support portion 21 is configured to be worn around the user's waist BW. The waist support portion 21 has a belt 25. The belt 25 can change the length of the waist support portion 21 around the waist BW and is used to secure the waist support portion 21 to the waist BW. The waist support portion 21 is composed of a hard core made of resin etc. and a member made of leather or cloth. Cases 36 for the actuator units 13R, 13L are attached to the right and left sides of the waist support portion 21. The waist support portion 21 and the cases 36 are attached such that they are rotatable relative to each other in one direction and the other direction about the imaginary line Li in the lateral direction of the user.

The jacket portion 22 is configured to be worn around the user's shoulder BS and chest BB. The jacket portion 22 has first attachments 26 and second attachments 27. The jacket portion 22 is coupled to the frame 23 by the first attachments 26. The jacket portion 22 is coupled to the waist support portion 21 by the second attachments 27. The jacket portion 22 is composed of a hard core made of resin etc. and a member made of leather or cloth.

The frame 23 is composed of pipes made of metal such as aluminum alloy, etc. The frame 23 has a main frame 28, a right subframe 29R, and a left subframe 29L. The main frame 28 has a padding member 30 that is configured to contact the user's back. The right subframe 29R is a pillar-like member connecting the main frame 28 and a part of the right actuator unit 13R, and the left subframe 29L is a pillar-like member connecting the main frame 28 and a part of the left actuator unit 13L. The upper end of the right subframe 29R is coupled to a part of the main frame 28, and the lower end of the right subframe 29R is coupled to the case 36 for the right actuator unit 13R. The upper end of the left subframe 29L is coupled to a part of the main frame 28, and the lower end of the left subframe 29L is coupled to the case 36 for the left actuator unit 13L. The right and left actuator units 13R, 13L and the frame 23 of the first brace 11 are thus connected together, and the right and left actuator units 13R, 13L and the frame 23 (first brace 11) are not allowed to be displaced relative to each other.

The backpack portion 24 is attached to the back of the main frame 28. The backpack portion 24 is also called a control box and has a box shape. The backpack portion 24 stores the control device 15, a power supply (battery) 20, etc. The power supply 20 supplies necessary electric power to devices such as the control device 15 and the right and left actuator units 13R, 13L.

The right and left second braces 12R, 12L are configured to be worn around the user's right and left thighs BF. The second brace 12R for the right thigh BF and the second brace 12L for the left thigh BF are symmetrical in shape but have the same configuration. The second brace 12L (12R) has a pad 31 and a belt 32. The pad 31 has a plate shape and is composed of a hard core made of resin etc. The belt 32 is composed of a member made of leather or cloth. The actuator unit 13L has an assist arm 37, and the pad 31 is attached to the assist arm 37. The pad 31 is configured to contact the front side of the thigh BF. The belt 32 is attached to the pad 31. The belt 32 can change the length of the second brace 12L (12R) around the thigh BF and is used to secure the pad 31 and the assist arm 37 to the thigh BF.

The right and left actuator units 13R, 13L are attached to the right and left sides of the waist support portion 21. The right actuator unit 13R and the left actuator unit 13L are symmetrical in shape but have the same configuration and the same functions. The right actuator unit 13R and the left actuator unit 13L can operate independently of each other, and can not only perform the same operation synchronously but also perform different operations.

The right actuator unit 13R is attached between the first brace 11 and the right second brace 12R. Specifically, the right actuator unit 13R is attached between the waist support portion 21 and frame 23 (right subframe 29R) of the first brace 11 and the right second brace 12R. The left actuator unit 13L is attached between the first brace 11 and the left second brace 12L. Specifically, the left actuator unit 13L is attached between the waist support portion 21 and frame 23 (left subframe 29L) of the first brace 11 and the left second brace 12L.

The right actuator unit 13R includes a configuration for applying torque about the imaginary line Li to the user through the first brace 11 and the right second brace 12R. The left actuator unit 13L includes a configuration for applying torque about the imaginary line Li to the user through the first brace 11 and the left second brace 12L. As described above, the torque that is applied in the assist operation is the "assist torque." The assist device 10 can support the rotational movements of the thighs BF with respect to the waist BW of the user by the assist torques that are output from the right and left actuator units 13R, 13L.

The actuator unit 13R includes an actuator 35, the case 36 that stores the actuator 35, and an assist arm 37. The actuator 35 includes an electric motor and a transmission mechanism that transmits rotational torque generated by the electric motor to the assist arm 37. A shaft 37a is fitted in the upper end of the assist arm 37. The axis of the shaft 37a matches the imaginary line Li. The shaft 37a extends in the case 36 such that it can rotate about the imaginary line Li. The assist arm 37 can thus rotate with respect to the first brace H about the imaginary line Li. The second brace 12R is attached to the lower end of the assist arm 37. As shown in FIGS. 3 and 4, the assist arm 37 is configured to extend along the user's thigh BF and to rotate with the thigh BF.

The actuator 35 rotationally drives the shaft 37a about the imaginary line Li and transmits the rotational torque to the shaft 37a. The rotational torque from the actuator 35 is thus used as torque for rotating the assist arm 37 about the imaginary line Li. The torque for rotating the assist arm 37 is applied as the assist torque to the user through the first brace 11 and the second brace 12R. The actuator 35 thus generates the assist torque. Like the actuator unit 13R, the actuator unit 13L also includes an actuator 35, the case 36 that stores the actuator 35, and an assist arm 37, and the actuator 35 generates the assist torque. The actuators 35 of the actuator units 13R, 13L are controlled by the control device 15.

Each assist arm 37 has an upper arm portion 40 and a lower arm portion 41. The upper arm portion 40 is rotatably attached to the case 36 and is rotated by the rotational torque from the actuator 35. The lower arm portion 41 is coupled to the lower end of the upper arm portion 40 and rotates with the upper arm portion 40. The second braces 12R, 12L are attached to the lower arm portions 41.

Figure 5:
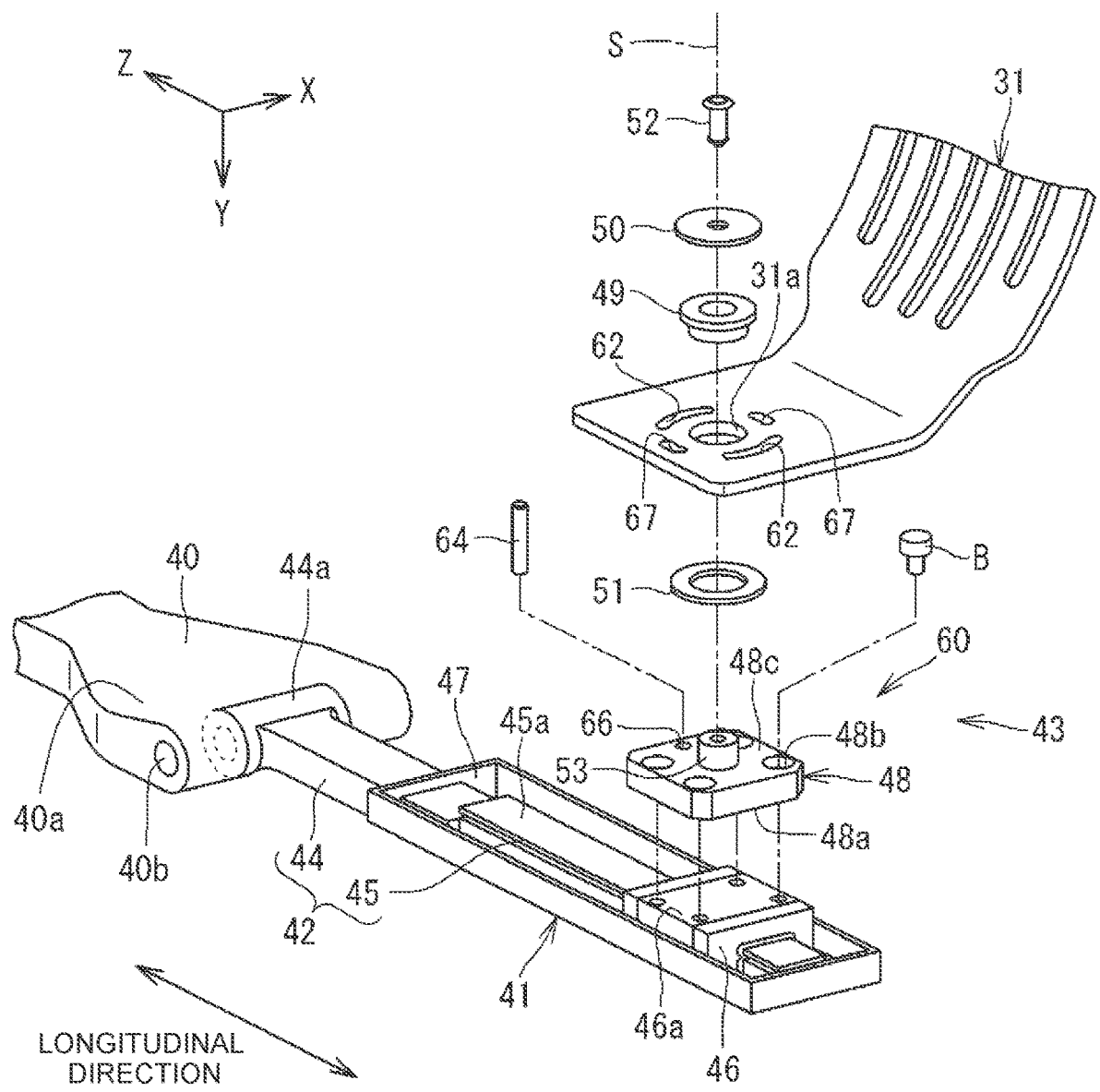
FIG. 5 is an enlarged exploded perspective view of a lower arm portion.

FIG. 5 is an enlarged exploded perspective view of the lower arm portion 41. The assist arm 37 of the actuator unit 13R and the assist arm 37 of the actuator unit 13L are symmetrical in shape but have the same configuration. The lower arm portion 41 of the assist arm 37 of the actuator unit 13L will be described.

The lower arm portion 41 includes an arm body 42 coupled to the upper arm portion 40 and a holding portion 43 that rotatably holds the second brace 12L. The arm body 42 includes a link member 44 coupled to the upper arm portion 40, and a guide rail 45. A male hinge 44a is attached to the upper end of the link member 44, and a female hinge 40a is attached to the lower end of the upper arm portion 40. The male hinge 44a is joined to the female hinge 40a via a hinge pin 40b.

The guide rail 45 is an elongated member on which a moving block 46 runs. The upper end of the guide rail 45 is coupled to the lower end of the link member 44. The guide rail 45 extends in the longitudinal direction of the lower arm portion 41 shown by a double arrow in FIG. 5, and guides the moving block 46 such that the moving block 46 can move in the longitudinal direction of the lower arm portion 41. The guide rail 45 and the moving block 46 are formed using what is called a linear guide. Accordingly, there are many steel balls between the moving block 46 and the guide rail 45, and these steel balls allow the moving block 46 to smoothly move on the guide rail 45. A cover 47 that protects the guide rail 45 and the moving block 46 is provided around the guide rail 45 of the lower arm portion 41.

The holding portion 43 includes the moving block 46, a base member 48, a bush 49, an outer washer 50, an inner washer 51, and a rivet 52. As described above, the moving block 46 can move in the longitudinal direction of the lower arm portion 41 as it runs on a guide surface 45a of the guide rail 45. The base member 48 is a member having a quadrilateral plate shape and made of an aluminum alloy. The base member 48 is fixed to a support surface 46a of the moving block 46. The base member 48 is fixed to the moving block 46 with one surface 48a of the base member 48 in contact with the support surface 46a. The base member 48 has counterbore bolt holes 48b in its four corners. The bolt holes 48b extend through the base member 48 from the one surface 48a to a base surface 48c that is the opposite surface of the base member 48 from the one surface 48a. The bolt holes 48b are open to the base surface 48c. Fixing bolts B for fixing the base member 48 to the moving block 46 are inserted through the bolt holes 48b. A rotation shaft 53 for retaining the pad 31 is provided on the base surface 48c of the base member 48. The rotation shaft 53 is integral with the base member 48 and protrudes from the base surface 48c. The pad 31 is a member having a plate shape and made of an aluminum alloy.

Figure 6:
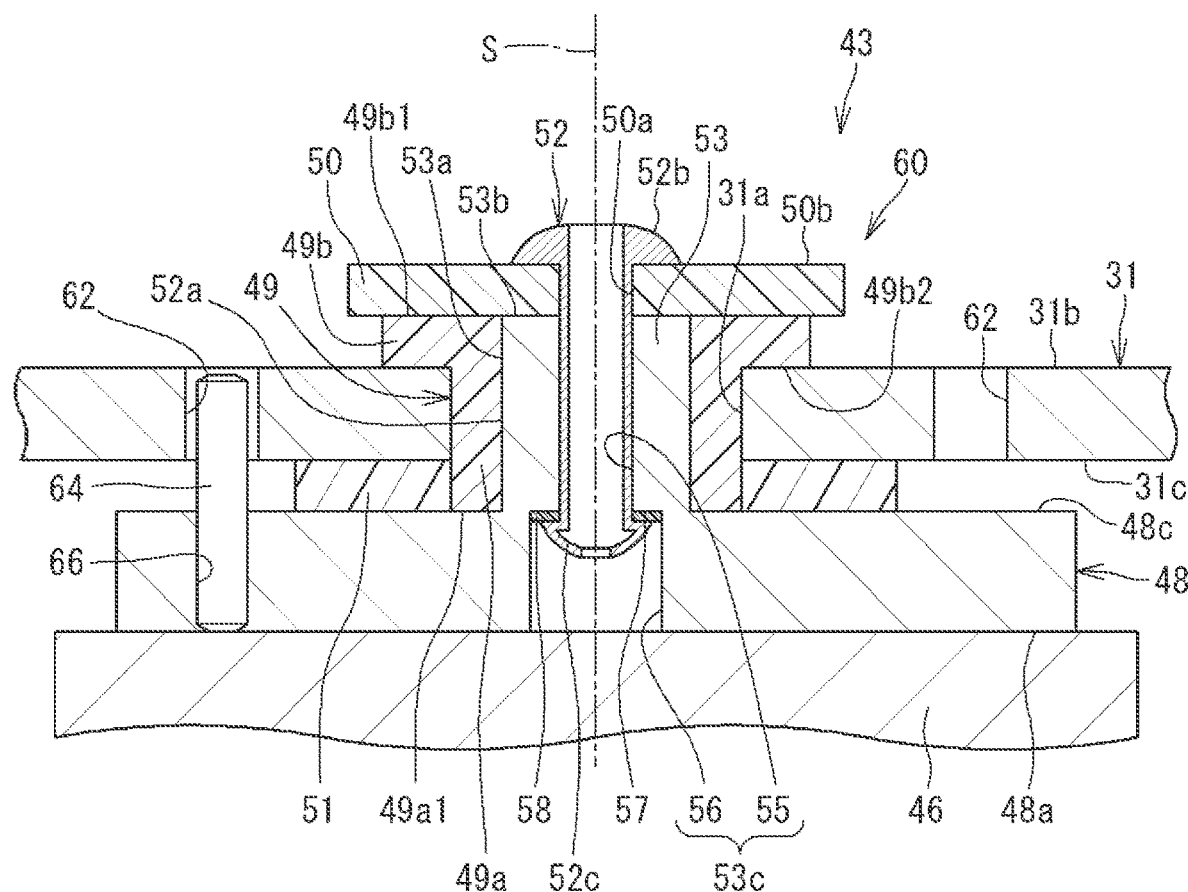
FIG. 6 is a sectional view of a holding portion.

FIG. 6 is a sectional view of the holding portion 43. FIG. 6 illustrates a section taken along a plane including the axis S of the rotation shaft 53 and parallel to the longitudinal direction to the lower arm portion 41. As shown in FIG. 6, the rotation shaft 53 is passed through a hole 31a of the pad 31. The axis S of the rotation shaft 53 is approximately perpendicular to the base surface 48c. The one surface 48a and the base surface 48c are approximately parallel. The base surface 48c extends in the longitudinal direction of the lower arm portion 41. The bush 49 is a cylindrical member made of resin etc. and has a cylindrical portion 49a and a flange portion 49b. The bush 49 is fitted on the rotation shaft 53 and is located between an inner peripheral surface of the hole 31a and an outer peripheral surface 53a of the rotation shaft 53. The flange portion 49b is provided at one end of the cylindrical portion 49a. One surface 49b1 of the flange portion 49b is approximately flush with a tip end face 53b of the rotation shaft 53. The other surface 49a1 of the cylindrical portion 49a is in contact with the base surface 48c. The axial length of the bush 49 is therefore approximately the same as the axial length of the rotation shaft 53. The other surface 49b2 of the flange portion 49b is in contact with one surface 31b of the pad 31. The inner washer 51 is an annular member made of resin and is fitted on the bush 49 and the rotation shaft 53. The inner washer 51 is in contact with the other surface 31c of the pad 31 and in contact with the base surface 48c, and is located between the pad 31 and the base member 48.

The outer washer 50 is an annular member made of resin and is in contact with the tip end face 53b of the rotation shaft 53 and the one surface 49b1 of the flange portion 49b. The outer washer 50 thus holds the pad 31, the bush 49, and the inner washer 51 between the outer washer 50 and the base surface 48c. The rivet 52 is passed through a hole 50a of the outer washer 50. The rivet 52 is a cylindrical member made of stainless steel and has a cylindrical portion 52a, a head 52b, and a riveted portion 52c. The rivet 52 has the head 52b at one end of the cylindrical portion 52a and has the riveted portion 52c at the other end of the cylindrical portion 52a. The rivet 52 is inserted from the hole 50a of the outer washer 50 and is passed through a central hole 53c of the rotation shaft 53.

The central hole 53c of the rotation shaft 53 has a small-diameter hole 55 and a large-diameter hole 56. The small-diameter hole 55 is open to the tip end face 53b, and the large-diameter hole 56 is open to the one surface 48a. The small-diameter hole 55 and the large-diameter hole 56 are connected by a step surface 57. The head 52b of the rivet 52 is in contact with an outer surface 50b of the outer washer 50. The riveted portion 52c of the rivet 52 is located in the large-diameter hole 56. An internal washer 58 is disposed between the riveted portion 52c and the step surface 57. The internal washer 58 is an annular member made of resin and is interposed between the riveted portion 52c and the step surface 57.

The rivet 52 is fixed so as to sandwich the outer washer 50 and (the rotation shaft 53 of) the base member 48 between the head 52b and the riveted portion 52c. The rivet 52 thus restrains the outer washer 50 from being separated from the tip end face 53b of the rotation shaft 53. In this manner, the pad 31 together with the bush 49 and the inner washer 51 is held between the outer washer 50 and the base surface 48c.

The pad 31 is retained by the base member 48 with the inner washer 51 interposed between the pad 31 and the base surface 48c. The pad 31 is thus retained facing the base surface 48c. This configuration can suppress direct contact between the pad 31 and the base member 48, both made of an aluminum alloy, and allows the pad 31 to rotate smoothly. The rotation shaft 53 is passed through the hole 31a of the pad 31. The pad 31 is therefore supported such that it can rotate about the axis S. That is, the rotation shaft 53, the bush 49, the outer washer 50, the inner washer 51, the rivet 52, and the internal washer 58 form a pad support portion 60 that rotatably supports the pad 31 such that the pad 31 faces the base surface 48c. Clearances between the sliding contact portions of the rotation shaft 53, bush 49, outer washer 50, inner washer 51, rivet 52, and internal washer 58 are set as appropriate such that the pad 31 can rotate with respect to the arm body 42.

As described above, as the holding portion 43 has the moving block 46, the lower arm portion 41 includes the holding portion 43 that can move in the longitudinal direction of the lower arm portion 41. Moreover, as the holding portion 43 has the pad support portion 60, the holding portion 43 rotatably holds the second brace 12L including the pad 31. According to the assist device 10 of the present embodiment, the second brace 12L to be worn on the thigh BF is held by the holding portion 43. The second brace 12L is thus held such that it can move and rotate with respect to the lower arm portion 41 (assist arm 37). Accordingly, the second brace 12L (12R) can be moved or rotated according to the body shape and movements of the user. This configuration reduces a pressing or rubbing feeling the second brace 12L (12R) causes on the thigh BF when the assist force is applied from the assist device 10, and thus reduces a weird feeling or discomfort that is given to the user.

Referring to FIGS. 5 and 6, the pad 31 has a pair of slits 62 around the hole 31a. The slits 62 extend in the circumferential direction about the axis S that is the rotation center of the pad 31 (second brace 12L) with a central angle in the range of about 45 degrees to about 50 degrees. The slits 62 are located symmetrically with respect to the hole 31a as the one surface 31b is viewed in plan.

A pin member 64 fixed to the base member 48 is inserted in one of the slits 62. The pin member 64 is fixed in a hole 66 of the base member 48 and protrudes from the base surface 48c. This slit 62 extends in the circumferential direction about the axis S. Accordingly, as the pad 31 is rotated, the pin member 64 inserted in the slit 62 moves with respect to the pad 31 along the slit 62. The pad 31 is thus rotated with the pin member 64 inserted in the slit 62. The rotation range of the pad 31 is therefore limited by the slit 62. With this configuration, the rotation range of the second brace 12L can be limited to a necessary range by the pin member 64 fixed to the base member 48 and the slit 62 of the pad 31, and ease of handling is therefore less likely to be affected by excessive rotation of the second brace 12L.

As shown in FIG. 5, the pad 31 further has a pair of exposure holes 67 between the slits 62. The exposure holes 67 are holes for exposing the bolt holes 48b that are open to the base surface 48c. The exposure holes 67 can expose the bolt holes 48b in the base surface 48c and the fixing bolts B inserted through the bolt holes 48b as the pad 31 is rotated. With this configuration, even though the base surface 48c is covered by the pad 31, the fixing bolts B can be inserted into and removed from the bolt holes 48b that are open to the base surface 48c through the exposure holes 67.

Another Embodiment

Figure 7:
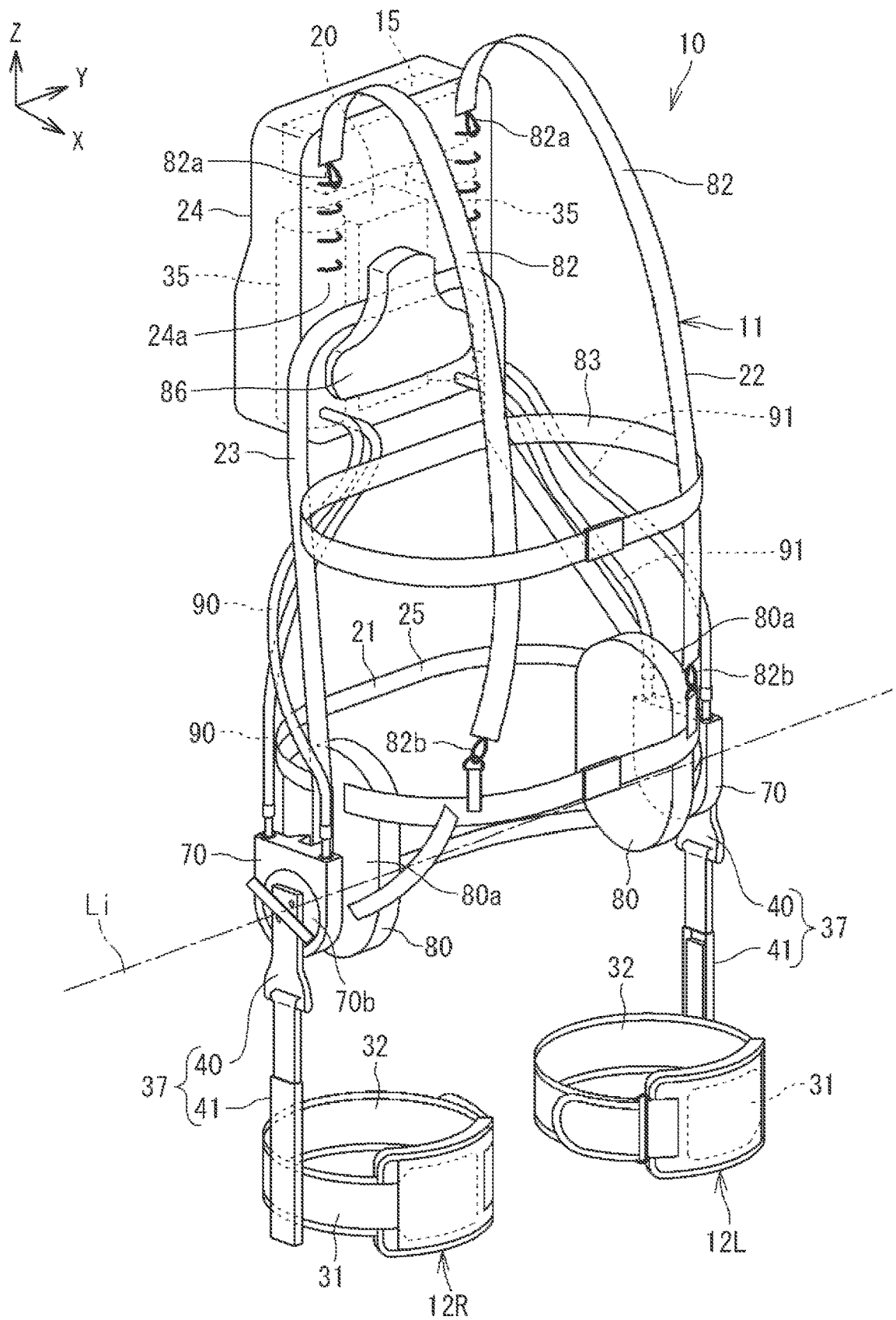
FIG. 7 is a perspective view illustrating the overall configuration of an assist device according to another embodiment.
Figure 8:
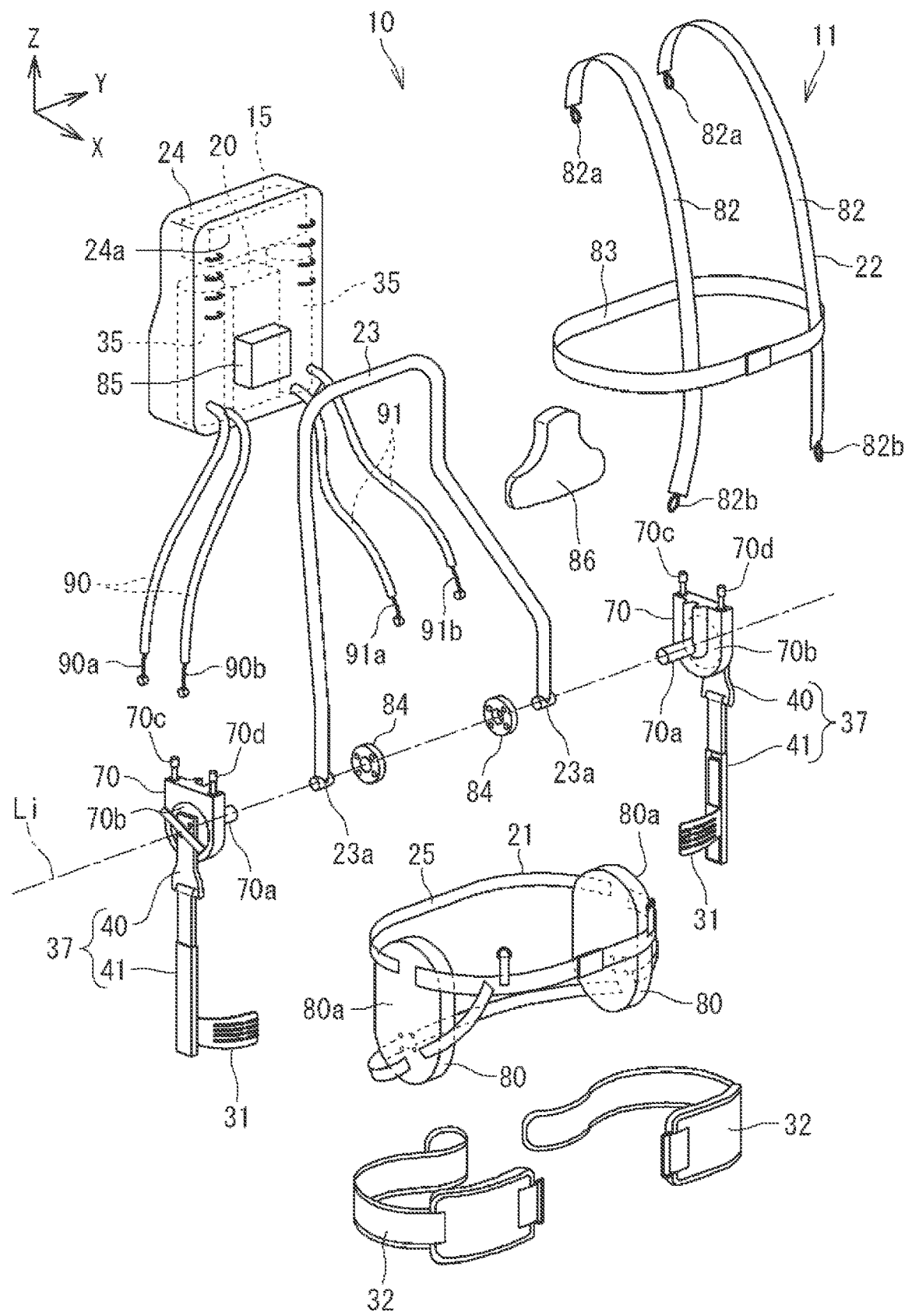
FIG. 8 is an exploded perspective view of the assist device of FIG. 7.
Figure 9:
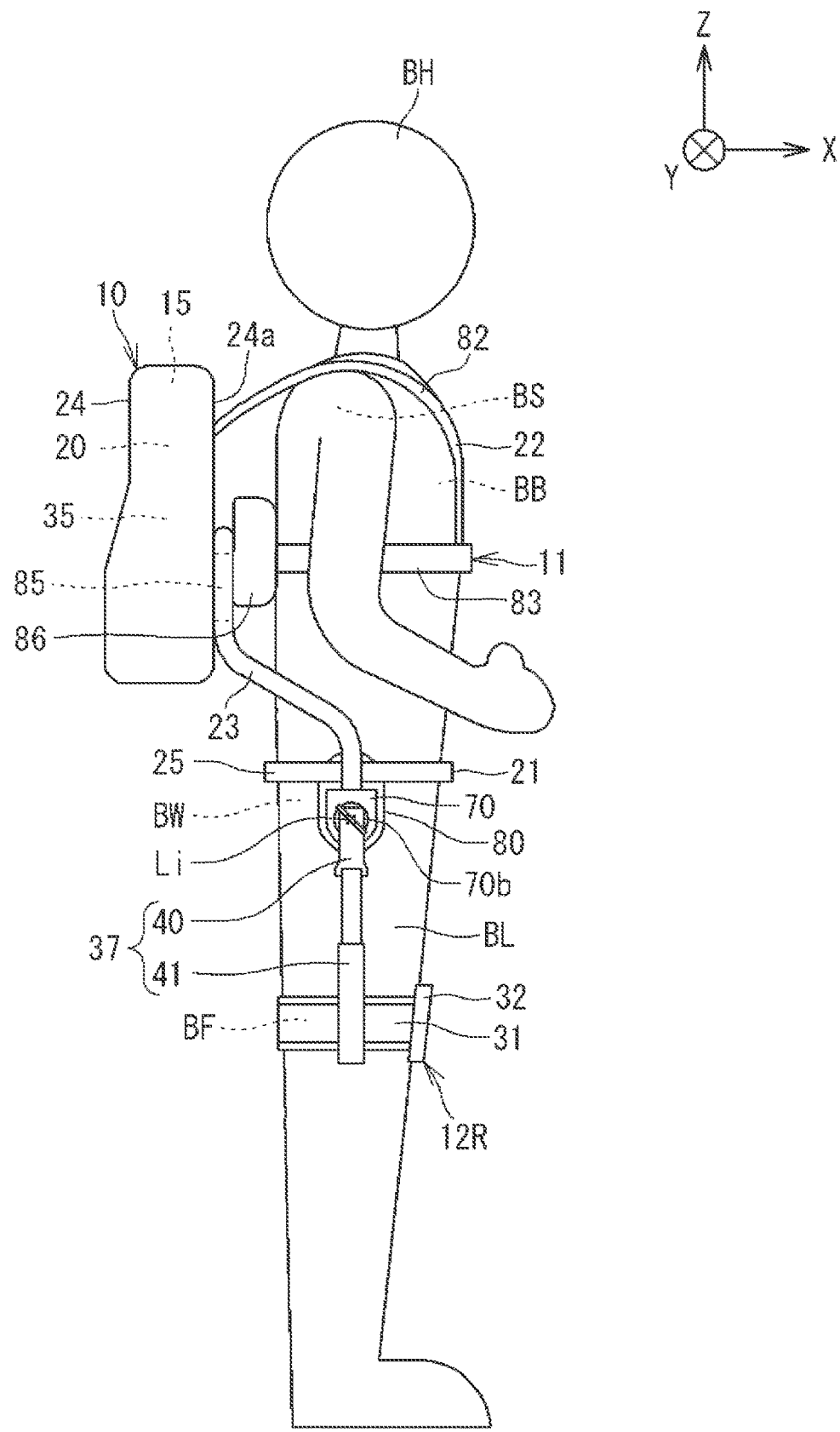
FIG. 9 is a side view of a user wearing the assist device of FIG. 7.

FIG. 7 is a perspective view illustrating the overall configuration of the assist device 10 according to another embodiment. FIG. 8 is an exploded perspective view of the assist device 10 of FIG. 7. FIG. 9 is a side view of a user wearing the assist device 10 of FIG. 7. In FIG. 9, the assist device 10 is schematically illustrated, and the user wearing the assist device 10 is in the upright posture.

The assist device 10 of the present embodiment is different from the above embodiment in that the actuators 35 that generate the torque (assist torque) for rotating the assist arms 37 are stored in the backpack portion 24. In the present embodiment as well, the assist device 10 includes the first brace 11 configured to be worn on the user's upper body including the waist BW, and the second braces 12R, 12L configured to be worn on the user's right and left thighs BF. Each of the second braces 12R, 12L and the assist arms 37 (upper arm portions 40 and lower arm portions 41) to which the second braces 12R, 12L are attached has a configuration similar to that of the above embodiment.

The first brace 11 includes the waist support portion 21, the jacket portion 22, the frame 23, and the backpack portion 24 as in the above embodiment, and further includes a pair of rotation mechanisms 70. The waist support portion 21 is configured to be worn around the user's waist BW. The waist support portion 21 includes the belt 25 and a pair of waist side pads 80. The belt 25 is used to secure the waist side pads 80 to the waist BW. The waist side pads 80 are provided on the right and left sides of the belt 25. The waist side pads 80 are members in the form of a pad and made of an elastic foam sheet etc. The rotation mechanisms 70 are fixed to outer side surfaces 80a of the waist side pads 80. The assist arms 37 are fixed to the rotation mechanisms 70. Each rotation mechanism 70 includes a configuration for rotating the assist arm 37. One of the rotation mechanisms 70 is fixed to the right waist side pad 80, and the other is fixed to the left waist side pad 80.

The jacket portion 22 configured to be worn around the user's shoulder BS and chest BB has a pair of shoulder belts 82 and a chest belt 83. Each shoulder belt 82 has an upper attachment 82a and a lower attachment 82b. The shoulder belts 82 are coupled to the backpack portion 24 by the upper attachments 82a. The shoulder belts 82 are coupled to the waist support portion 21 by the lower attachments 82b. The chest belt 83 is coupled to the shoulder belts 82 by, e.g., sewing the chest belt 83 on the shoulder belts 82 such that the chest belt 83 crosses the shoulder belts 82. The chest belt 83 is configured to be worn around the user's chest BB.

The frame 23 composed of a pipe made of metal such as aluminum alloy is configured to pass between the user's back and the backpack portion 24. The frame 23 connects together the rotation mechanisms 70 fixed to the outer side surfaces 80a of the waist side pads 80. Each rotation mechanism 70 is provide with a fixing shaft 70a, and cylindrical portions 23a through which the fixing shafts 70a are inserted are provided at both ends of the frame 23. The rotation mechanisms 70 and the cylindrical portions 23a are provided with anti-rotation stoppers so as not to rotate relative to each other. The rotation mechanisms 70 therefore do not rotate relative to the frame 23. Annular fixing members 84 are fixed to the outer side surfaces 80a of the waist side pads 80. The fixing shafts 70a are inserted through and fixed in the cylindrical portions 23a and the fixing members 84. The rotation mechanisms 70 are thus fixed to the frame 23 and to the outer side surfaces 80a of the waist side pads 80. At this time, the axes of the fixing shafts 70a match the imaginary line Li in the lateral direction of the user passing through the user's waist BW.

A spacer 85 and a back pad 86 are provided on a front surface 24a of the backpack portion 24 attached behind the frame 23. The spacer 85 is disposed between the front surface 24a and the back pad 86. The frame 23 is sandwiched between the front surface 24a and the back pad 86. The waist support portion 21, the jacket portion 22, the frame 23, the backpack portion 24, and the rotation mechanisms 70 are thus connected together, and the rotation mechanisms 70 and the frame 23 are not allowed to be displaced relative to each other.

The pair of actuators 35 is stored in the backpack portion 24, in addition to the control device 15 and the power supply 20. One of the actuators 35 is an actuator that generates torque for rotating the right assist arm 37, and the other is an actuator that generates torque for rotating the left assist arm 37.

A pair of wires 90 and a pair of wires 91 extend from the backpack portion 24. Each wire 90 is covered by a protective tube and is connected to the right rotation mechanism 70. Each wire 91 is covered by a protective tube and is connected to the left rotation mechanism 70. The one actuator 35 transmits torque to the right rotation mechanism 70 via the wires 90, and the other actuator 35 transmits torque to the left rotation mechanism 70 via the wires 91. The one actuator 35 has a drive pulley (not shown) for driving the wires 90. The one actuator 35 withdraws one of ends 90a, 90b of the wires 90 and advances the other end by rotating the drive pulley. Similarly, the other actuator 35 withdraws one of ends 91a, 91b of the wires 91 and advances the other end by rotating a drive pulley for driving the wires 91.

The right assist arm 37 is fixed to the right rotation mechanism 70, and the left assist arm 37 is fixed to the left rotation mechanism 70. The right rotation mechanism 70 has a driven pulley 70b. The driven pulley 70b can rotate in one direction and the other direction about the imaginary line Li in the lateral direction of the user. The right assist arm 37 is fixed to the driven pulley 70b such that it can rotate with the driven pulley 70b. A drive wire (not shown) is wound around the driven pulley 70b. One end of the drive wire is guided by a connection end 70c and is connected to the end 90a of the wire 90. The other end of the drive wire is guided by a connection end 70d and is connected to the end 90b of the wire 90.

When either one end or the other end of the drive wire is pulled, the driven pulley 70b is rotated accordingly. Accordingly, when the one actuator 35 rotates the drive pulley to withdraw one of the ends 90a, 90b of the wires 90, the driven pulley 70b is rotated according to the movements of the wires 90. When the driven pulley 70b is rotated, the right assist arm 37 is rotated about the imaginary line Li accordingly. The rotational torque of the one actuator 35 is thus transmitted to the right rotation mechanism 70 via the wires 90 and is used as torque for rotating the right assist arm 37.

The left rotation mechanism 70 has a configuration similar to that of the right rotation mechanism 70. Accordingly, when a driven pulley 70b of the left rotation mechanism 70 is rotated according to the movements of the wires 91, the left assist arm 37 is rotated about the imaginary line Li accordingly. The rotational torque of the other actuator 35 is thus transmitted to the left rotation mechanism 70 via the wires 91 and is used as torque for rotating the left assist arm 37. With this configuration, the assist device 10 of the present embodiment can also support the rotational movements of the thighs BF with respect to the waist BW of the user.

Since the assist device 10 of the present embodiment has the assist arms 37 having a configuration similar to that of the above embodiment, the assist device 10 of the present embodiment reduces a pressing or rubbing feeling the second braces 12R, 12L cause on the thighs BF when the assist force is applied from the assist device 10, and thus reduces a weird feeling or discomfort that is given to the user.

Others

Figure 10:
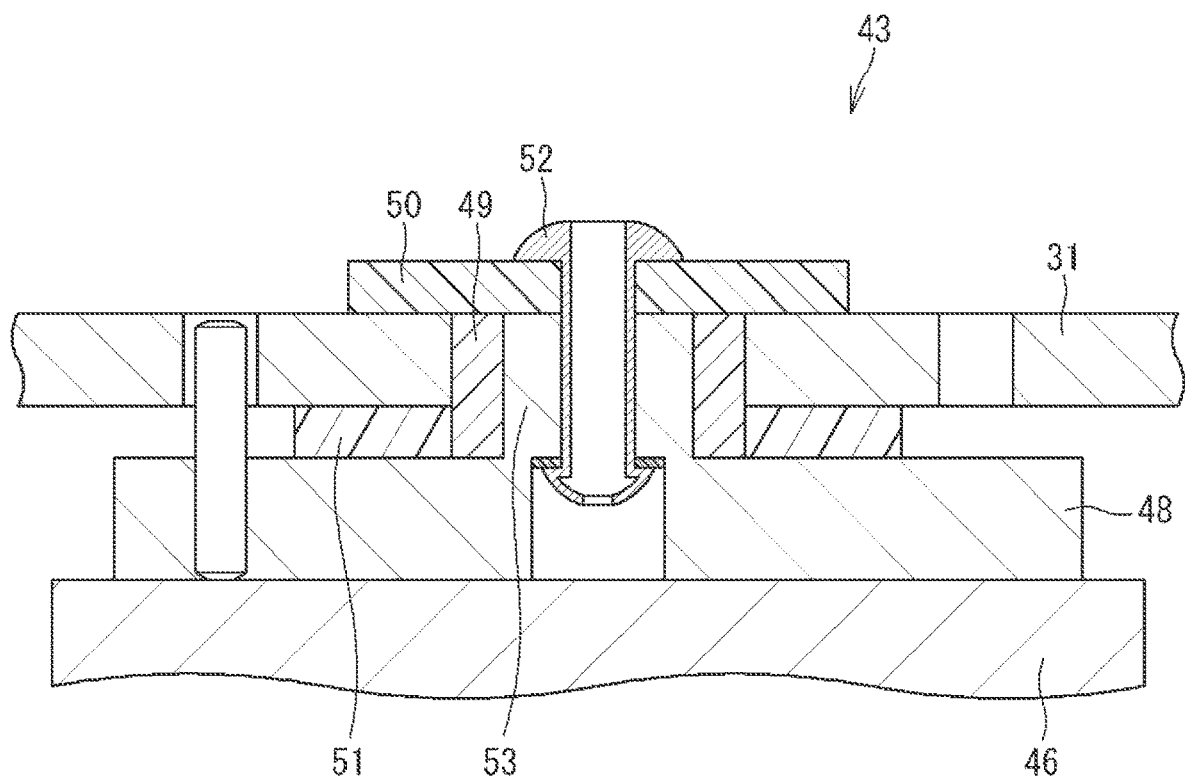
FIG. 10 is a sectional view of a holding portion according to a modification.

The disclosure is not limited to the above embodiments. For example, in the above embodiments, the bush 49 included in the holding portion 43 has the flange portion 49b. However, as shown in, e.g., FIG. 10, the bush 49 may not have the flange portion 49b. In the above embodiments, the components of the assist device 10 are made of metal or resin. However, the materials of the components of the assist device 10 are not limited. For example, in the above embodiments, the pad 31 is made of an aluminum alloy. However, the pad 31 may be made of resin. In the above embodiments, the bush, the washers, etc. are made of resin. However, the bush, the washers, etc. may be made of metal.

The scope of the disclosure is defined by the scope of the claims and is intended to include all modifications that fall within the scope of the claims and equivalents thereof.

What is claimed is:

1. An assist device, comprising:
   a first brace configured to be worn on at least a waist of a user;
   an arm configured to extend along a thigh of the user and to rotate with respect to the first brace;
   an actuator configured to generate torque that rotates the arm; and
   a second brace provided on the arm and configured to be worn on the thigh, wherein the arm includes an arm body and a holding portion, the holding portion being provided on the arm body such that the holding portion is movable in a longitudinal direction of the arm body, and the holding portion holding the second brace such that the second brace is rotatable, the second brace includes a pad having a plate shape, the arm body includes a guide rail extending in the longitudinal direction of the arm body, the holding portion includes a moving block, a base member, and a pad support portion, the moving block being configured to run on the guide rail in the longitudinal direction of the arm body, the base member being fixed to the moving block and including a base surface extending in the longitudinal direction, and the pad support portion supporting the pad such that the pad is rotatable with the pad facing the base surface, the pad has a slit extending in a circumferential direction about a rotation center of the second brace, and the holding portion further includes a pin member protruding from the base surface and inserted in the slit.

2. The assist device according to claim 1, wherein the base member has a bolt hole being open to the base surface and having in place a bolt that fixes the base member to the moving block, and the pad has an exposure hole configured to expose the bolt hole.

3. The assist device according to claim 1, wherein the pad is configured to contact a front side of the thigh of the user, and includes a hole, an axis of the hole being coincident with the rotation center of the second brace, and the base member includes a rotation shaft protruding from and integral with the base surface, the rotation shaft passing through the hole of the pad.

4. The assist device according to claim 3, wherein the rotation shaft includes a central hole including a small-diameter hole and a large-diameter hole connected by a step surface, and the pad support portion includes a bush fitted on the rotation shaft and located between an inner peripheral surface of the hole of the pad and an outer peripheral surface of the rotation shaft, an outer washer in contact with a tip end face of the rotation shaft and a first end of the bush, an inner washer sandwiched between the pad and the base member, and a rivet including a head in contact with an outer surface of the outer washer and a riveted portion located in the large-diameter hole, the rivet being fixed so as to sandwich the outer washer and the rotation shaft of the base member between the head and the riveted portion such that the pad, the bush, and the inner washer is held between the outer washer and the base surface of the base member.

5. The assist device according to claim 4, wherein the bush includes a flange portion at the first end of the bush, a first surface of the flange being substantially flush with the tip end face of the rotation shaft and a second surface of the flange being in contact with the pad, and a second end of the bush is in contact with the base surface.

\* \* \* \* \*